(12) United States Patent
Park et al.

(10) Patent No.: US 11,052,039 B2
(45) Date of Patent: Jul. 6, 2021

(54) COSMETIC COMPOSITION EFFECTIVE FOR CELL MOISTURIZATION, INTERCELLULAR MOISTURIZATION AND SKIN-BARRIER MOISTURIZATION CONTAINING PLANT EXTRACT

(71) Applicants: Coseedbiopharm Co., Ltd., Cheongju-si (KR); COSMECCA KOREA CO., LTD., Chungcheongbuk-do (KR)

(72) Inventors: Sung Min Park, Cheongju-si (KR); Jung No Lee, Cheongju-si (KR); Hwa Sun Ryu, Cheongju-si (KR); Na Ri Kim, Cheongju-si (KR); Young Kwon Cha, Yongin-si (KR); In Young Na, Gwangju-si (KR); Hang Eui Cho, Yongin-si (KR)

(73) Assignees: COSEEDBIOPHARM CO., LTD., Cheongju-si (KR); COSMECCA KOREA CO., LTD., Chungcheongbuk-do (KR)

( * ) Notice: Subject to any disclaimer, the term of this patent is extended or adjusted under 35 U.S.C. 154(b) by 9 days.

(21) Appl. No.: 16/749,528

(22) Filed: Jan. 22, 2020

(65) Prior Publication Data

US 2020/0237645 A1   Jul. 30, 2020

(51) Int. Cl.
*A61K 36/00* (2006.01)
*A61K 8/9789* (2017.01)
*A61Q 19/00* (2006.01)
*A61K 8/9728* (2017.01)

(52) U.S. Cl.
CPC .......... *A61K 8/9789* (2017.08); *A61K 8/9728* (2017.08); *A61Q 19/007* (2013.01)

(58) Field of Classification Search
CPC ....................................................... A61K 36/00
USPC ......................................................... 424/725
See application file for complete search history.

(56) References Cited

FOREIGN PATENT DOCUMENTS

| KR | 10-2001-0022183 A | 3/2001 |
| KR | 10-2009-0131399 A | 12/2009 |
| KR | 10-2011-0045662 A | 5/2011 |
| KR | 10-2014-0072291 A | 6/2014 |

*Primary Examiner* — Michael V Meller
(74) *Attorney, Agent, or Firm* — Vorys, Sater, Seymour and Pease LLP; Mih Suhn Koh (57) ABSTRACT

Provided is a cosmetic composition for skin moisturization containing a hydrolyzate extract obtained by adding a protease to the fruit of *Cicer arietinum*, a *Rhododendron chrysanthum* leaf extract and a *Tricholoma matsutake* extract. The cosmetic composition exhibits excellent effects on cell moisturization, intercellular moisturization and skin-barrier moisturization. In addition, the cosmetic composition is harmless to the human body and has excellent stability because it uses natural substances.

1 Claim, 5 Drawing Sheets

COSMETIC COMPOSITION EFFECTIVE FOR CELL MOISTURIZATION, INTERCELLULAR MOISTURIZATION AND SKIN-BARRIER MOISTURIZATION CONTAINING PLANT EXTRACT

BACKGROUND OF THE INVENTION

Field of the Invention

The present invention relates to a cosmetic composition effective for cell moisturization, intercellular moisturization and skin-barrier moisturization containing a plant extract, and more particularly to a moisturizing cosmetic composition containing a hydrolyzate extract obtained by adding a protease to the fruit of *Cicer arietinum*, a *Rhododendron chrysanthum* leaf extract and a *Tricholoma matsutake* extract.

Description of the Related Art

Skin is an organ that serves as a protective membrane that protects the human body from the external environment, and functions to prevent the loss of biological components such as water and electrolytes from the human body, and at the same time, to prevent invasion of harmful substances from the outside. The skin is divided into three layers, namely the epidermis, dermis and subcutaneous fatty tissue, sequentially from the outside.

The moisture content of the skin is about 70% in the dermal layer, but decreases toward the epidermal layer and is thus about 10% to 30% in the epidermal layer. When the moisture content of the epidermal layer is 10% or less, the skin becomes rough and the body loses the protective function thereof, thus causing aging. The epidermis is divided into four layers, namely the stratum corneum, stratum granulosum, stratum spinosum and stratum basale, sequentially from the outside. The cells of the stratum corneum serve as bricks, and the lipids between the cells in the stratum corneum serve as mortar to form a skin barrier.

In addition, there is a high concentration of natural moisturizing factor (NMF) in the keratinocytes of healthy people, and NMF functions to increase the moisture content of skin. However, despite this function of the skin, exogenous aging, caused by external factors such as indoor heating, polluted air and ultraviolet rays, endogenous aging and removal of components constituting the skin caused by physicochemical stimuli derived from friction, shaving, cleansing and the like, may cause a moisture imbalance and thus dry skin. In order to prevent these phenomena, skin moisturizer is considered important, and various studies are being conducted into improving skin moisturization efficacy at the cellular level.

It is considerably important to maintain suitable moisture content in the keratinocyte layers in the skin. For this purpose, cosmetics are added with ingredients similar to sebum, NMF ingredients, or moisturizers such as polyols. For example, glycerin, sorbitol or the like, having three or more hydroxyl groups (OH groups), as water-soluble polyols, exhibit excellent moisturizing capability, but are very sticky and thus are unpleasant for the user. Propylene glycol, 1,3-butylene glycol and the like, having two hydroxyl groups, may cause side effects on the skin. In addition, other natural moisturizing factors such as sodium pyrrolidone carboxylate (PCA-Na), sodium lactate and urea have a problem of impairing the emulsion stability of cosmetics due to the strong electrolyte nature thereof, and amino acids, collagen, elastin, and the like have also moisturizing ability, but the moisturizing ability thereof is limited. Thus, there is a need for the development of natural cosmetic compositions in order to increase the skin moisturization capability.

PRIOR ART

Patent Document (Patent Document 1) Korean Patent Laid-open No. 10-2001-0022183 (published on Mar. 15, 2001) discloses a composition for protecting skin containing *Cicer arietinum*.

(Patent Document 2) Korean Patent Laid-open No. 10-2009-0131399 (published on Dec. 29, 2009) discloses a cosmetic composition having anti-inflammatory and anti-irritant effects containing a mixed extract of *Xanthium strumarium, Rhododendron chrysanthum* and burdock.

(Patent Document 3) Korean Patent Laid-open No. 10-2011-0045662 (published on May 4, 2011) discloses an anti-inflammatory and antioxidant cosmetic composition containing green tea polysaccharide and a *Tricholoma matsutake* extract.

(Patent Document 4) Korean Patent Laid-open No. 10-2014-0072291 (published on Jun. 13, 2014) discloses an anti-wrinkling pharmaceutical or cosmetic composition containing a *Tricholoma matsutake* extract as an active ingredient.

SUMMARY OF THE INVENTION

Therefore, the present invention has been made in order to solve the problems of chemicals used for conventional moisturizing cosmetic compositions, and it is an object of the present invention to develop and provide a cosmetic composition containing natural substances that is harmless to the human body, has excellent stability and is effective in moisturizing.

In accordance with the present invention, the above and other objects can be accomplished by the provision of a cosmetic composition for skin moisturization containing a hydrolyzate extract obtained by adding a protease to the fruit of *Cicer arietinum*, a *Rhododendron chrysanthum* leaf extract and a *Tricholoma matsutake* extract.

In the cosmetic composition of the present invention, the moisturizing preferably includes any one selected from cell moisturization, intercellular moisturization and skin-barrier moisturization.

In the cosmetic composition of the present invention, the extract is preferably obtained through any one extraction method selected from solvent extraction, supercritical extraction and ultrasonic extraction.

In this case, the solvent extraction is preferably carried out using any one extraction solvent selected from the group consisting of water, anhydrous or hydrous lower alcohol having 1 to 4 carbon atoms, propylene glycol, butylene glycol, glycerin, acetone, ethyl acetate, chloroform, butyl acetate, diethyl ether, dichloromethane, hexane and a mixture thereof.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The present invention provides a cosmetic composition for skin moisturization containing a hydrolyzate extract obtained by adding a protease to the fruit of *Cicer arietinum*, a *Rhododendron chrysanthum* leaf extract and a *Tricholoma matsutake* extract.

*Cicer arietinum* is a soybean perennial grass, which is called "chickpea" or "chick pea" because has a protruding portion like a chick's beak in the middle. *Cicer arietinum* has been cultivated since 7,500 BC and is one of the earliest grown beans in human history. It generally grows well in dry climates and is cultivated in Central America, India, Africa and the like. In particular, *Cicer arietinum* is rich in vitamins and minerals, and has a high calcium content and thus is effective for alleviating anemia and improving immunity, and also contributes to cholesterol reduction.

*Rhododendron chrysanthum* is a dicotyledonous plant of the *Rhododendron* family and is called a "cure-all plant" in folk remedies because it has notable efficacy in treating many kinds of conditions such as high blood pressure, low blood pressure, diabetes, neuralgia and lack of vitality (stamina). *Rhododendron chrysanthum* grows in colonies in alpine districts such as Mt. Seorak and Mt. Baekdu, and is also distributed in China, Japan and Russia.

*Tricholoma matsutake* is a fungus that belongs to the Agaricales and Tricholomataceae, and requires a growing condition native to pine. *Tricholoma matsutake* can be found in northern China, the Korean peninsula, Japan and the like, and is rich in minerals such as potassium and magnesium, as well as various nutrients such as beta glucan and vitamins, and is thus known to be useful in chemotherapy. In addition, *Tricholoma matsutake* contains about 2 times more potassium and about 3 times more calcium than natural *Tricholoma matsutake*, and thus contributes to bone and joint health.

In the cosmetic composition of the present invention, the moisturization preferably includes any one selected from cell moisturization, intercellular moisturization and skin-barrier moisturization. The experiment described below showed that the cosmetic composition for skin moisturization containing a hydrolyzate extract, a *Rhododendron chrysanthum* leaf extract and a *Tricholoma matsutake* extract according to the present invention exhibits excellent effects of moisturizing skin cells and membranes through identification of aquaporin-3 and claudin-1 expression. In addition, the cosmetic composition exhibits an excellent effect on moisture retention capacity. Thus, various formulations having a skin-moisturizing effect can be provided using a moisturizing cosmetic composition containing a hydrolyzate extract obtained by adding a protease to the fruit of *Cicer arietinum*, a *Rhododendron chrysanthum* leaf extract and a *Tricholoma matsutake* extract as active ingredients.

Meanwhile, aquaporin (AQP) is a membrane protein that is responsible for the transport of water in cell membranes, and is known as a water passage that selectively regulates the entry and exit of water molecules into and out of cells while interfering with the movement of ions and solutes. There are 13 AQPs (AQP-0 to AQP-12) in mammals, among which AQP-1, AQP-2, AQP-4, AQP-5 and AQP-8 are known to have a main function of selectively carrying water, while AQP-3, AQP-7, AQP-9 and AQP-10 are known to carry glycerol and other small solutes. In particular, AQP-3 has been reported to be expressed in the keratinocytes of the stratum basale of the epidermis, and activation of AQP-3 in keratinocytes is expected to deliver moisture deep into the skin to obtain excellent skin-moisturizing effects.

Meanwhile, the moisturizing ability in the skin is closely related to the function of the skin barrier, and the skin barrier function can be destroyed by aging or external stimuli. Damage to the skin barrier directly reduces skin moisture and causes wrinkle formation, and many studies have been conducted to solve these problems. Tight junctions (TJ) between keratinocytes, which are the main cells constituting the stratums, are a key factor.

Tight junctions function to prevent the loss of moisture and invasion of harmful substances inside the human body by linking intercellular adhesion. Occludin, claudin, ZO-1 and the like are known as tight-junction proteins, and most tight-junction proteins are present between the granulosa cell layers of the epidermis. Among them, the transmembrane protein, claudin-1 has a ring-shaped structure that tightly fills the space between cells to regulate the intercellular space and thereby effectively block the movement passage of moisture. Recent studies have reported that claudin-1 plays an important role owing to the skin barrier function thereof, which affects skin moisturization.

In the cosmetic composition of the present invention, the extract is preferably obtained through any one extraction method selected from solvent extraction, supercritical extraction and ultrasonic extraction. In this case, the solvent extraction is preferably carried out using any one extraction solvent selected from the group consisting of water, anhydrous or hydrous lower alcohol having 1 to 4 carbon atoms, propylene glycol, butylene glycol, glycerin, acetone, ethyl acetate, chloroform, butyl acetate, diethyl ether, dichloromethane, hexane and a mixture thereof. In particular, it can be seen through the following experiment that an ethanol extract of a hydrolyzate obtained by adding a protease to the fruit of *Cicer arietinum*, a *Rhododendron chrysanthum* leaf ethanol extract and a *Tricholoma matsutake* ethanol extract have an excellent moisturizing effect (not shown) and that, when the extracts are mixed in the same ratio, an excellent moisturizing effect can be obtained.

Meanwhile, in the present invention, the mixed extract is preferably present in an amount of 0.0001 to 30.0% by weight, based on the total weight of the cosmetic composition, more preferably 0.01 to 10% by weight based on the total weight of the cosmetic composition. When the content of the mixed extract is less than 0.0001% by weight, the skin-moisturizing effect is insignificant, and when the content of the extract exceeds 30.0% by weight, a remarkable effect compared to the increase in content cannot be obtained.

Meanwhile, the ingredients contained in the cosmetic composition of the present invention may include ingredients commonly used in cosmetic compositions, for example, conventional adjuvants such as antioxidants, stabilizers, solubilizers, vitamins, pigments and flavors, and carriers, in addition to the mixed extract of the present invention as active ingredients.

The cosmetic composition of the present invention may be prepared in any formulation conventionally prepared in the art and may be, for example, formulated into a solution, suspension, emulsion, paste, gel, cream, lotion, powder, soap, surfactant-containing cleansing agent, oil, powder foundation, emulsion foundation, wax foundation, pack, massage cream, spray or the like, but is not limited thereto. More specifically, the cosmetic composition may be prepared into a formulation such as a toner, lotion, nutritive cream, massage cream, essence, eye cream, cleansing cream, cleansing foam, cleansing water, pack, spray or powder.

When the formulation of the cosmetic composition of the present invention is a paste, cream or gel, the carrier ingredient may be an animal oil, vegetable oil, wax, paraffin, starch, tragacanth, cellulose derivative, polyethylene glycol, silicone, bentonite, silica, talc or zinc oxide.

When the formulation of the cosmetic composition of the present invention is a solution or emulsion, the carrier ingredient may be a solvent, solubilizing agent or emulsifying agent, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan.

When the formulation of the cosmetic composition of the present invention is a suspension, the carrier ingredient may be a liquid diluent such as water, ethanol or propylene glycol, a suspending agent such as ethoxylated isostearyl alcohol, polyoxyethylene sorbitol ester or polyoxyethylene sorbitan ester, microcrystalline cellulose, aluminum metahydroxide, bentonite, agar or tragacanth or the like.

When the formulation of the cosmetic composition of the present invention is a powder or a spray, the carrier ingredient may be lactose, talc, silica, aluminum hydroxide, calcium silicate or polyamide powder. In particular, when the formulation is a spray, it may further include a propellant such as chlorofluorohydrocarbon, propane/butane or dimethyl ether.

When the formulation of the cosmetic composition of the present invention is a surfactant-containing cleansing agent, the carrier component may be aliphatic alcohol sulfate, aliphatic alcohol ether sulfate, sulfosuccinic acid monoester, isethionate, imidazolinium derivative, methyl taurate, sarcosinate, fatty acid amide ether sulfate, alkyl amido betaine, aliphatic alcohol, fatty acid glyceride, fatty acid diethanolamide, vegetable oil, lanolin derivative, ethoxylated glycerol fatty acid ester or the like.

When the cosmetic composition of the present invention is a soap, surfactant-containing cleansing formulation or surfactant-free cleansing formulation, it may be wiped off, peeled off or washed with water after being applied to the skin. Specifically, for example, the soap may include liquid soap, powdered soap, solid soap and oil soap, the surfactant-containing cleansing formulation may include a cleansing foam, cleansing water, cleansing towel and cleansing pack, and the surfactant-free cleansing formulation may include a cleansing cream, cleansing lotion, cleansing water and cleansing gel, but is not limited thereto.

Hereinafter, the configuration of the present invention will be described in more detail with reference to the following examples and experimental examples. The scope of the present invention is not limited to the examples and experimental examples, and includes modifications of the technical concept equivalent thereto.

Preparation Example 1: Preparation of Ethanol Extract of *Cicer arietinum* Fruit Hydrolyzate 100 g of a chickpea (*Cicer arietinum*) fruit was pulverized, and 600 ml of purified water and 0.1 g of a protease were added to the pulverized product and reacted at 50° C. for 3 hours. Then, 500 ml of 70% ethanol was added thereto, followed by immersion twice at a temperature of 25° C. for 48 hours and filtration through No. 2 filter paper (Whatman). Then, the resulting product was concentrated under reduced pressure to prepare an ethanol extract of a *Cicer arietinum* fruit hydrolysate.

Preparation Example 2: Preparation of Ethanol Extract of *Rhododendron chrysanthum* Leaf 100 g of leaves of *Rhododendron chrysanthum* dried in the shade were pulverized, 500 ml of 70% ethanol was added to the pulverized product, and then extraction was performed at 60° C. for 24 hours. Then, the extract was filtered through a 400 mesh (mesh) filter cloth and then filtered again through No. 2 filter paper (Whatman). Then, the resulting product was concentrated under reduced pressure to prepare a *Rhododendron chrysanthum* leaf ethanol extract.

Preparation Example 3: Preparation of Ethanol Extract of *Tricholoma matsutake*

100 g of *Tricholoma matsutake* were pulverized, 500 ml of 70% ethanol was added to the pulverized product, and then extraction was performed at 60° C. for 24 hours. Then, the extract was filtered through a 400 mesh (mesh) filter cloth and then filtered again through No. 2 filter paper (Whatman). Then, the resulting product was concentrated under reduced pressure to prepare a *Tricholoma matsutake* ethanol extract.

Example 1 and Comparative Examples 1 to 6: Preparation of Mixture of Ethanol Extract of *Cicer arietinum* Fruit Hydrolyzate, *Rhododendron chrysanthum* Leaf Ethanol Extract and *Tricholoma Matsutake* Ethanol Extract The ethanol extract of *Cicer arietinum* fruit hydrolysate, the *Rhododendron chrysanthum* leaf ethanol extract and the *Tricholoma matsutake* ethanol extract prepared in Preparation Examples 1 to 3 were mixed at the composition ratios shown in the following Table 1, and the mixtures were dissolved at a concentration of 100 mg/ml in DMSO which were used in the following experiments.

TABLE 1

| Ingredients | Example 1 | Comparative Example 1 | Comparative Example 2 | Comparative Example 3 | Comparative Example 4 | Comparative Example 5 | Comparative Example 6 |
|---|---|---|---|---|---|---|---|
| Ethanol extract of Cicer arietinum fruit hydrolysate | 1 | 3 | — | — | 1.5 | 1.5 | — |
| Rhododendron chrysanthum leaf ethanol extract | 1 | — | 3 | — | 1.5 | — | 1.5 |
| Tricholoma matsutake ethanol extract | 1 | — | — | 3 | — | 1.5 | 1.5 |

Experimental Example 1: Measurement of Cell Viability

In this experiment, the toxicity of the extracts or mixtures according to Example 1 and Comparative Examples 1 to 6 on the cells was evaluated. Cell viability was measured using MTT (3-(4,5-dimethylthiazol-2-yl)-2-5-diphenyl tetrazolium bromide) reagent.

Human keratinocytes (HaCaT, keratinocyte) were seeded at a concentration of $2 \times 10^4$ cells/well in 96-well plates and incubated at 37° C. and 5% $CO_2$ for 24 hours. The culture medium was removed, and the extracts or mixtures obtained in Example 1 and Comparative Examples 1 to 6 were serially diluted to a concentration of 1 to 100 µg/ml and incubated for 24 hours. Then, 20 µl of a MTT reagent solution dissolved at a concentration of 5 mg/ml was added thereto and reacted at 37° C. and 5% $CO_2$ for 2 hours. After completely removing the medium, the formed formazan was completely dissolved in 100 µl of DMSO and the absorbance was measured at 540 nm.

Figure 1:
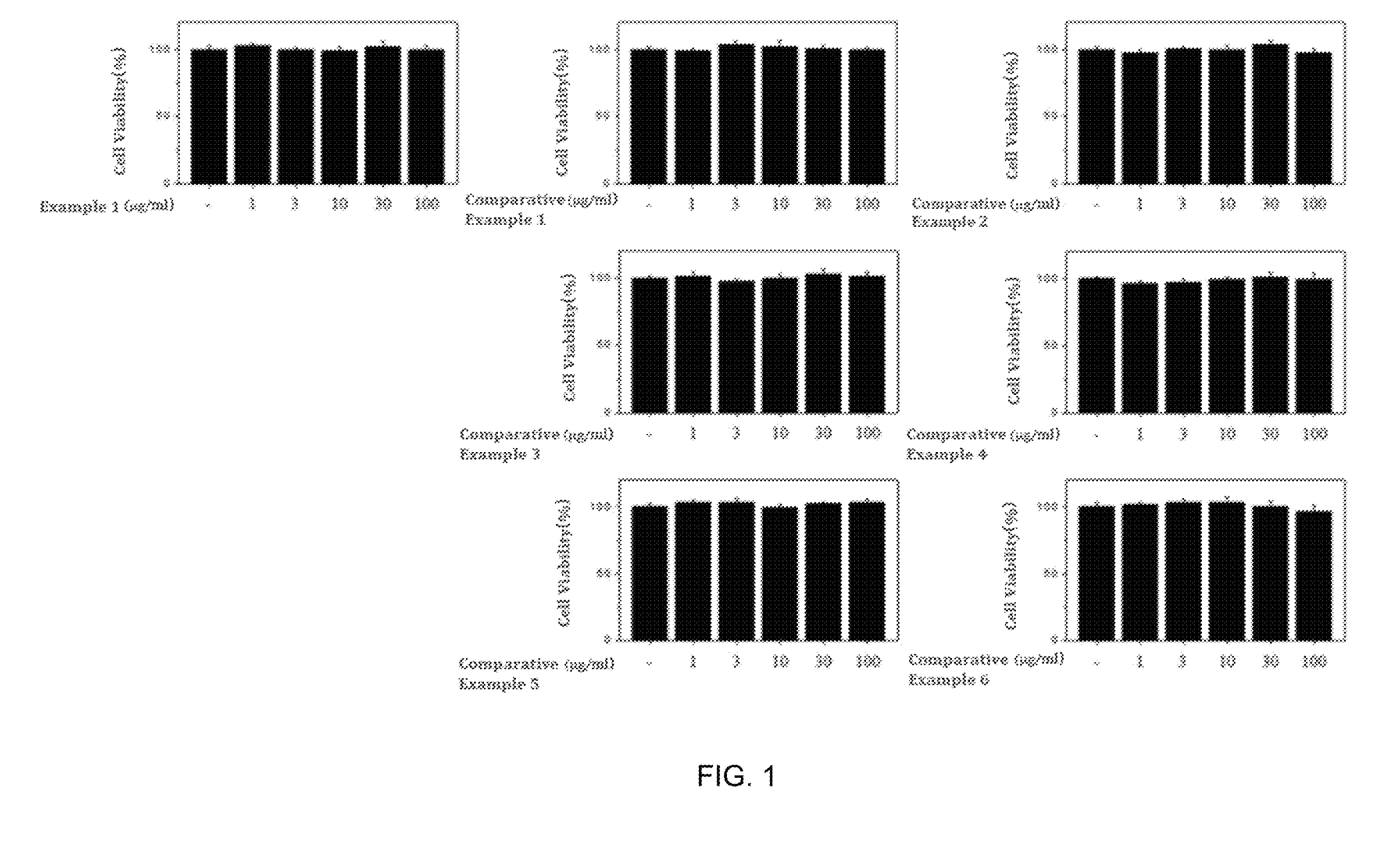
FIG. 1 shows the result of measurement of the toxicity of extracts or mixtures according to Example 1 and Comparative Examples 1 to 6 on cells.

The experimental result showed that the mixture according to Example 1 and the extracts or mixtures according to Comparative Examples 1 to 6 did not exhibit cytotoxicity up to a concentration of 100 µg/ml (FIG. 1). FIG. 1 shows the result of measurement of the toxicity of the extracts or mixtures according to Example 1 and Comparative Examples 1 to 6 on the cells.

Experimental Example 2: Determination of Cell Moisturization Effect Through Identification of Aquaporin-3 Expression In order to evaluate the moisturizing effect at the cellular level, the effects of the extracts or mixtures according to Example 1 and Comparative Examples 1 to 6 on AQP-3, which is a channel involved in intracellular water absorption, were determined. Dexamethasone was used as a positive control group.

HaCaT cells were seeded into 6-well plates, and the medium was treated at a concentration of 100 µg/ml with the extracts or mixtures according to Example 1 and Comparative Examples 1 to 6 when cell confluence reached 80%. Then, after incubation for 24 hours, the cells were collected and proteins were separated using a 1×cell lysis buffer. Subsequently, the protein was quantified through a BCA assay, and a predetermined amount of protein was electrophoresed on a 10% SDS-PAGE gel. Then, the protein was transferred to a PVDF membrane and blocked using 5% skim milk for 1 hour. Then, the resulting product was reacted with a primary antibody (AQP-3, Santacruz, USA) overnight at 4° C. and was then reacted with an HRP-bound secondary antibody at room temperature for 2 hours. Then, the cells were washed with TBS/T, and bands were identified using a Chemi Doc instrument and an ECL reaction kit. Each band was quantified based on the expression of beta-actin (β-actin) to calculate the amount of AQP-3 expression.

Figure 2:
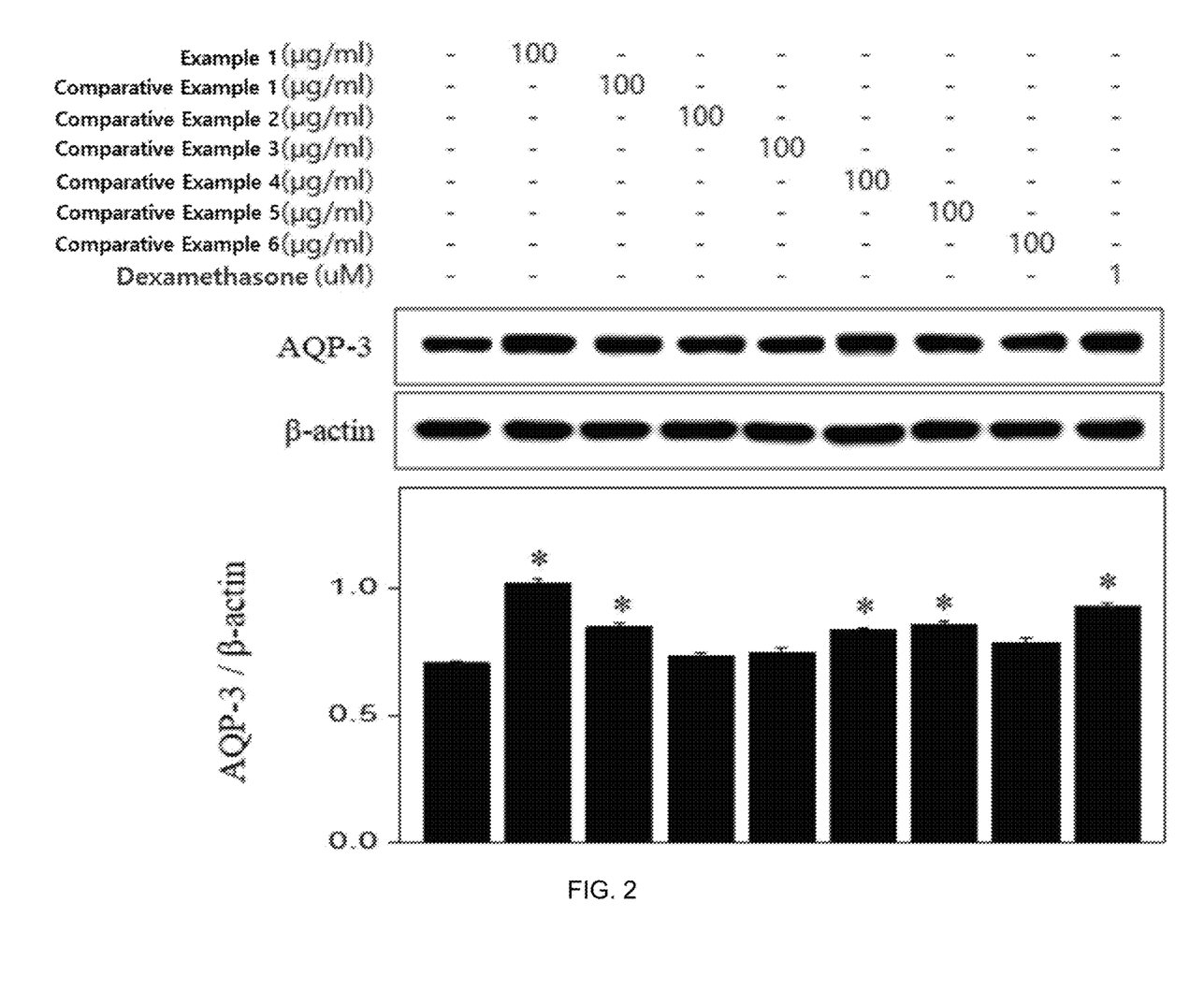
FIG. 2 shows the result of determination of the cell moisturization effect of the extracts or mixtures according to Example 1 and Comparative Examples 1 to 6 through the regulation of aquaporin-3 expression.

The experimental result showed that the positive control group, dexamethasone, increased AQP-3 expression by about 32%, and the mixture of Example 1 increased AQP-3 expression by about 44.7% at 100 µg/ml. The extract of Comparative Example 1 increased the expression of AQP-3 by 20.5%, the mixture of Comparative Example 4 increased the expression of AQP-3 by 18.7%, and the mixture of Comparative Example 5 increased the expression of AQP-3 by 21%. In addition, the extracts of Comparative Examples 2 and 3 and the mixture of Comparative Example 6 did not exhibit a significant increase in AQP-3 expression. These results indicated that the mixture of Example 1 was most effective for moisturizing the cells (FIG. 2). FIG. 2 shows the result of determination of the effects of the extracts or mixtures according to Example 1 and Comparative Examples 1 to 6 on cell moisturization through regulation of aquaporin-3 expression.

Experimental Example 3: Determination of Skin-Barrier

Moisturization Effect Through Identification of Claudin-1 Expression] The layer/membrane moisturizing effects of the extracts or mixtures according to Example 1 and Comparative Examples 1 to 6 on claudin-1, involved in water loss in the skin, was measured by the following method.

HaCaT cells were seeded into 6-well plates and the medium was treated at a concentration of 100 µg/ml with the extracts or mixtures according to Example 1 and Comparative Examples 1 to 6 when cell confluence reached 80%. Then, after incubation for 24 hours, the cells were collected, and proteins were separated using a 1×cell lysis buffer. Subsequently, the protein was quantified through BCA assay, and a predetermined amount of protein was electrophoresed on a 10% SDS-PAGE gel. Then, the protein was transferred to a PVDF membrane and blocked using 5% skim milk for 1 hour. Then, the resulting product was reacted with a primary antibody (claudin-1, cell signaling, USA) overnight at 4° C., and was then reacted with an HRP-bound secondary antibody at room temperature for 2 hours. Then, the cells were washed with TBS/T and bands were identified using a Chemi Doc instrument and an ECL reaction kit. Each band was quantified based on the expression of beta-actin (β-actin) to calculate the amount of claudin-1 expression.

Figure 3:
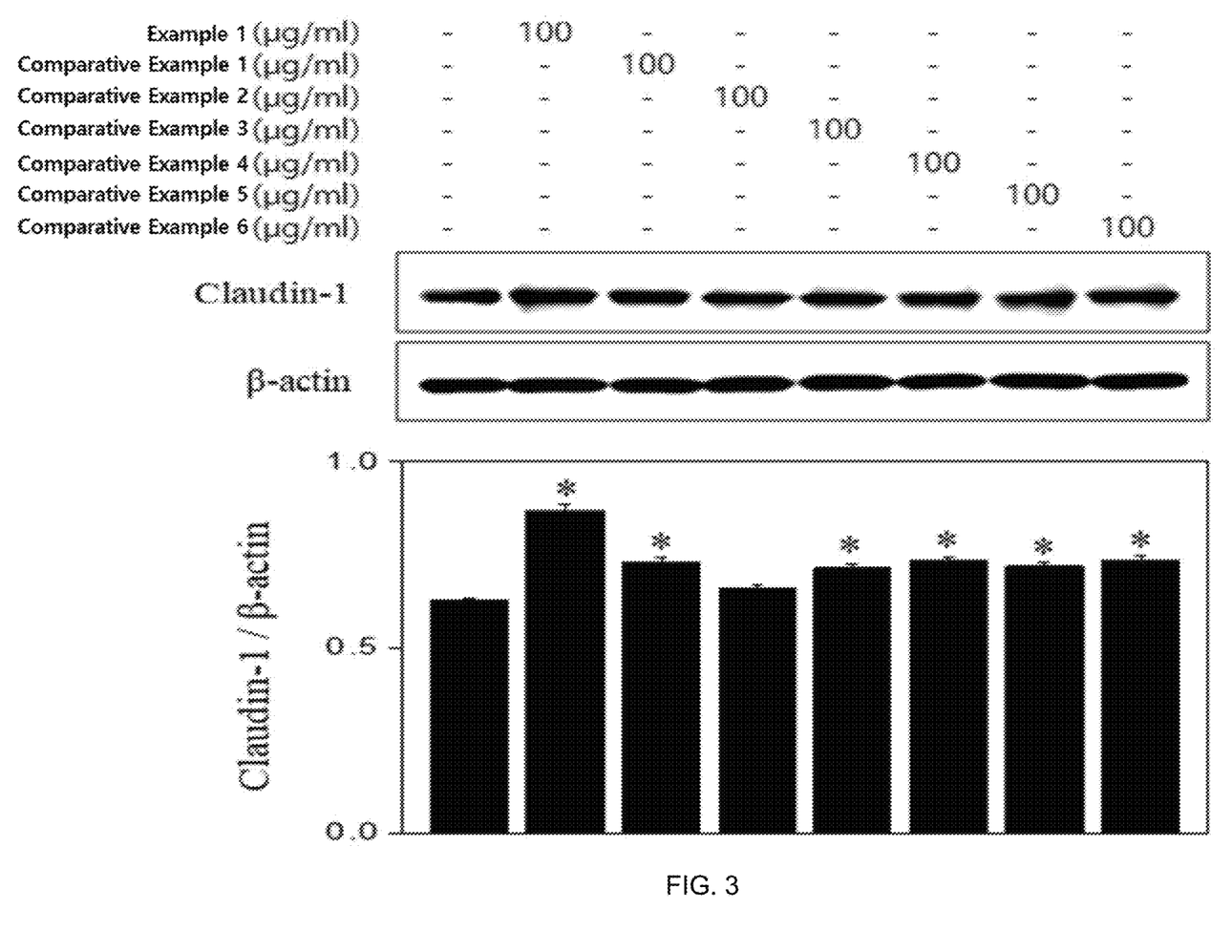
FIG. 3 shows the result of determination of the skin-barrier moisturization effect of the extracts or mixtures according to Example 1 and Comparative Examples 1 to 6 through regulation of claudin-1 expression.

The experimental result showed that the mixture of Example 1 increased the expression of claudin-1 by about 39.6% at a concentration of 100 µg/ml. Meanwhile, the extracts according to Comparative Examples 1 and 3 and the mixtures according to Comparative Examples 4 to 6 slightly increased the expression of claudin-1, and the extract of Comparative Example 2 exhibited a significant increase in the expression of claudin-1. Thus, it could be identified that the mixture of Example 1 was the most effective in moisturizing the skin layer/membrane (FIG. 3). FIG. 3 shows the result of determination of the skin-barrier moisturization effect of the extracts or mixtures according to Example 1 and Comparative Examples 1 to 6 through regulation of claudin-1 expression.

Experimental Example 4: Determination of Water-Holding Capacity

In this experiment, the water-holding capacity was measured using a solution, in which hyaluronic acid (HA) was added to the extracts or mixtures according to Examples 1 and Comparative Examples 1 to 6, as a comparative sample.

Figure 4:
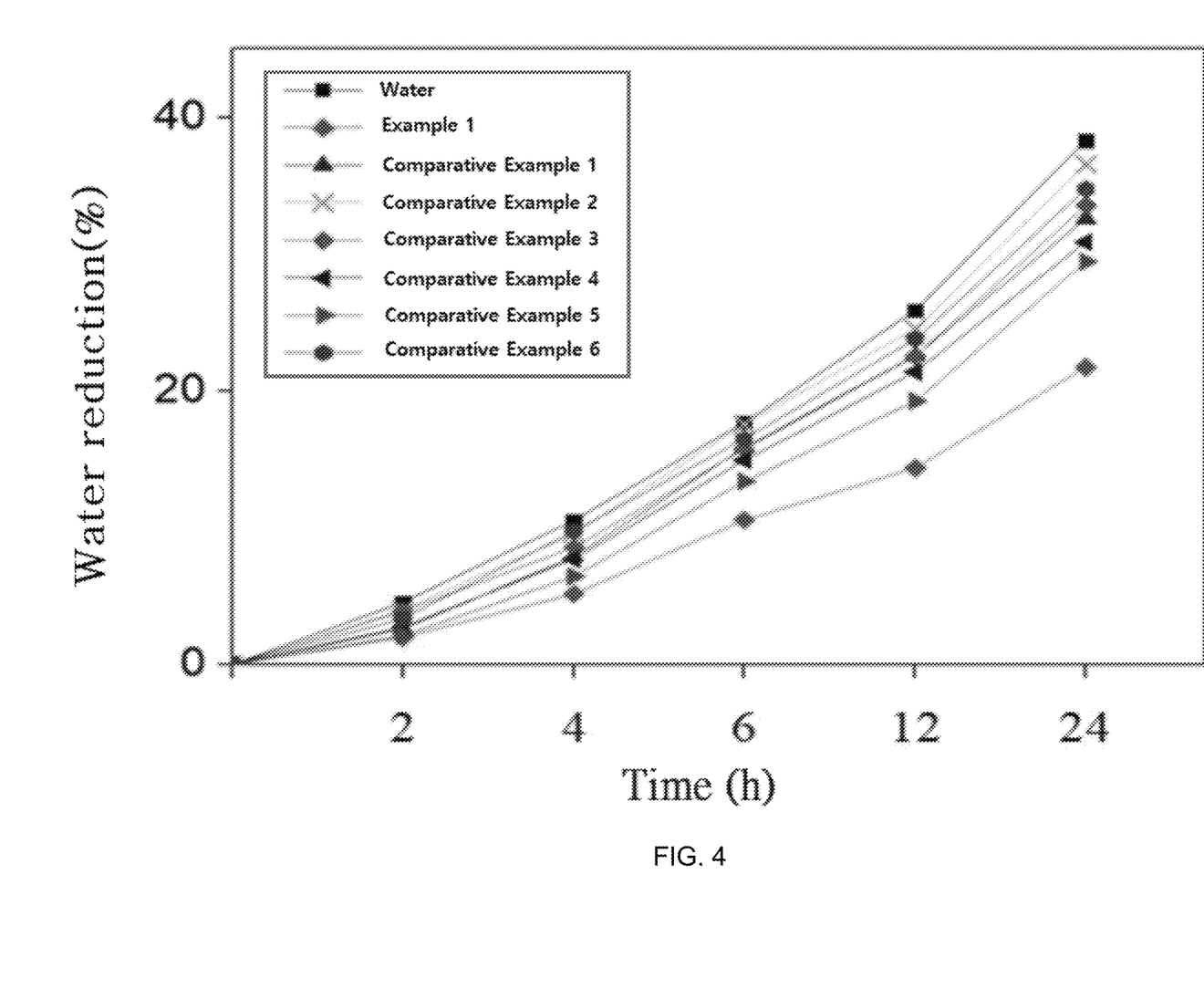
FIG. 4 shows the result of measurement of water reduction percentages of the extracts or mixtures according to Example 1 and Comparative Examples 1 to 6.

The experiment was carried out at a constant temperature, and 20 ml of each of the extracts or mixtures according to Example 1 and Comparative Examples 1 to 6 was placed in a petri dish. 0, 2, 4, 6, 12 and 24 hours later, the weight was measured with a precision balance and recorded in Table 2 below. The experimental results showed that, when comparing the mixture of Example 1 with the extracts or mixtures of Comparative Examples 1 to 6, the mixture of Example 1 lost the smallest amount of water to evaporation due to the excellent binding force with water (FIG. 4). FIG. 4 shows the result of measurement of the water reduction percentages of the extracts or mixtures according to Example 1 and Comparative Examples 1 to 6.

TABLE 2

| Time (Hour) | Vehicle (HA) | Example 1 | Comparative Example 1 | Comparative Example 2 | Comparative Example 3 | Comparative Example 4 | Comparative Example 5 | Comparative Example 6 |
|---|---|---|---|---|---|---|---|---|
| 0 | 22228.5 | 21770.1 | 23109.8 | 23551.5 | 23576.0 | 23109.8 | 24737.3 | 22793.4 |
| 2 | 21217.1 | 21336.2 | 22509.6 | 22612.5 | 22785.5 | 22623.8 | 24061.5 | 21907.9 |
| 4 | 19886.1 | 20648.1 | 21287.6 | 21301.4 | 21280.6 | 21621.1 | 22831.5 | 20843.7 |
| 6 | 18296.9 | 19474.2 | 19446.4 | 19419.2 | 19685.7 | 20018.4 | 21045.3 | 19203.4 |
| 12 | 16474.7 | 18640.2 | 17890.7 | 17768.7 | 17969.9 | 18660.2 | 19446.7 | 17651.7 |
| 24 | 13719.2 | 17041.4 | 15579.9 | 14941.5 | 15385.7 | 16306.7 | 17098.9 | 15145.8 |

Formulation Example 1: Preparation of Cosmetic Composition

A cosmetic composition containing 0.1% by weight of each of the ethanol extract of the *Cicer arietinum* fruit hydrolyzate, the *Rhododendron chrysanthum* leaf ethanol extract and the *Tricholoma matsutake* ethanol extract, as the mixture of Example 1, was prepared in accordance with the composition of Table 3 below, and is referred to "Formulation Example 1", and Comparative Formulation Example 1 was prepared as a control group.

TABLE 3

| Ingredients | Formulation Example 1 (wt %) | Comparative Formulation Example 1 (wt %) |
|---|---|---|
| Ethanol extract of *Cicer arietinum* fruit hydrolyzate | 0.1 | — |
| *Rhododendron chrysanthum* leaf ethanol extract | 0.1 | — |
| *Tricholoma matsutake* ethanol extract | 0.1 | — |
| 1,3-BG | 10.0 | 10.0 |
| Glycerin | 5.1 | 5.1 |
| Propylene glycol | 4.2 | 4.2 |
| Tocopheryl acetate | 3.0 | 3.0 |
| Liquid paraffin | 4.6 | 4.6 |
| Triethanolamine | 1.0 | 1.0 |
| Squalane | 3.1 | 3.1 |
| *Macadamia* nut oil | 2.5 | 2.5 |
| Polysorbate | 1.6 | 1.6 |
| Sorbitan sesquioleate | 1.6 | 1.6 |
| Propylparaben | 0.6 | 0.6 |
| Carboxyl vinyl polymer | 1.5 | 1.5 |
| Flavor | Trace | Trace |
| Preservative | Trace | Trace |
| Purified water | Balance | Balance |
| Total | 100.0 | 100.0 |

Experimental Example 5: Measurement of Trans-Epidermal Water Loss

In this experiment, the trans-epidermal water loss (TEWL) of Formulation Example 1 was determined. Trans-epidermal water loss means evaporation of the moisture inside the skin when the barrier function of the skin is lost. The assessment of water evaporation amount is expressed in $g/m^2$ (unit area/hour), meaning the amount of water evaporating in a unit area per hour.

The keratin was artificially removed from the skin inside a lower arm with a strapping method using a piece of tape, and Formulation Example 1 and Comparative Formulation Example 1 were applied to the skin. 1, 2, 4 and 6 hours after application, the amount of water evaporated from the skin was measured using a trans-epidermal water loss meter (Tewameter TM 210, Courage and Khazaka, Germany), and the result is shown in Table 4.

TABLE 4

| (Unit: $g/m^2/h$) | 0 h | 1 h | 2 h | 4 h | 6 h |
|---|---|---|---|---|---|
| Formulation Example 1 | 17.25 | 8.9 | 8.2 | 7.5 | 6.4 |
| Comparative Formulation Example 1 | 17.20 | 15.2 | 14.8 | 12.4 | 11.5 |

Figure 5:
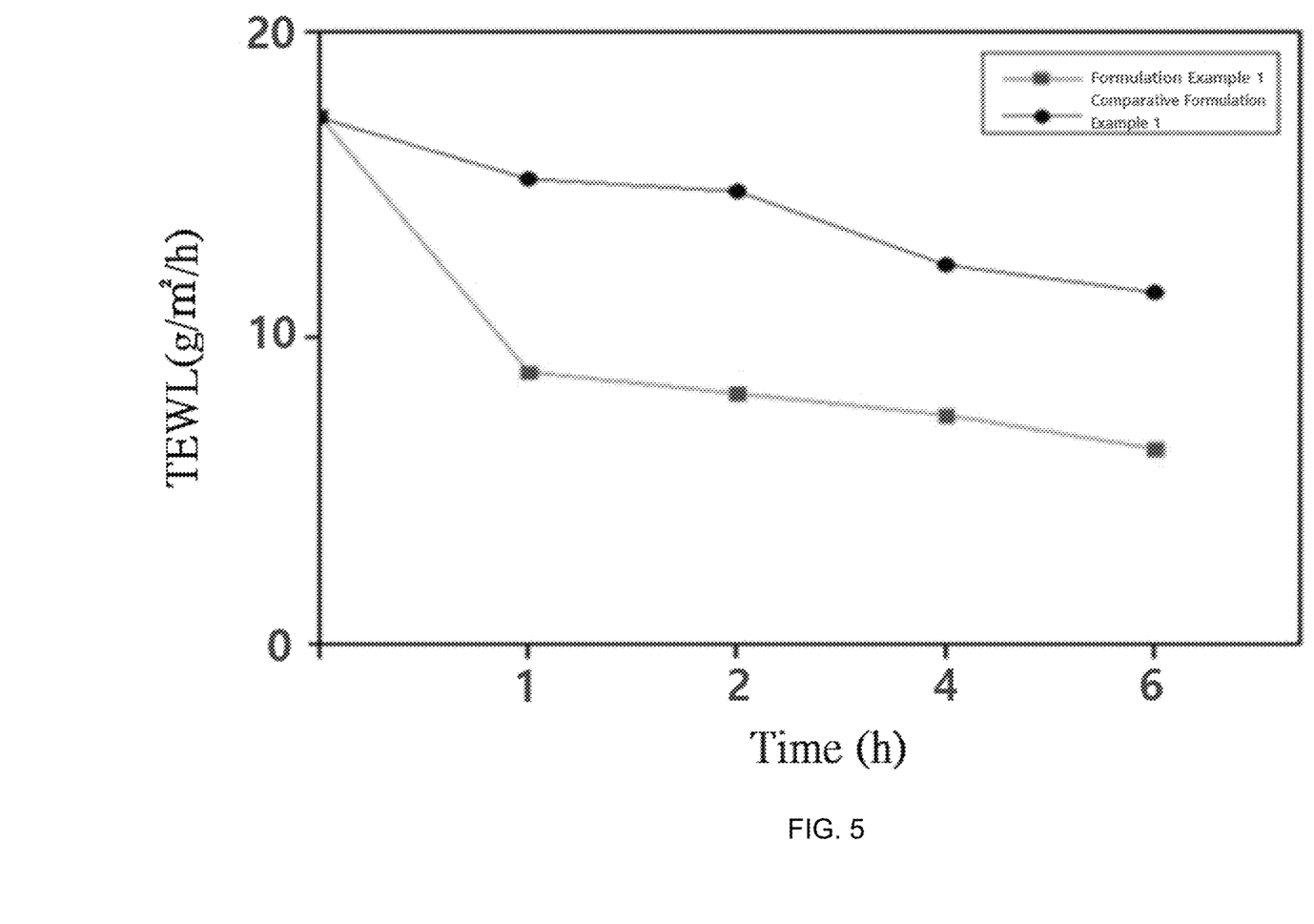
FIG. 5 shows the result of measurement of trans-epidermal moisture loss in Formulation Example 1 and Comparative Formulation Example 1.

The result showed that Formulation Example 1 exhibited considerably low trans-epidermal water loss compared to Comparative Formulation Example 1 (FIG. 5). FIG. 5 shows the result of measurement of trans-epidermal moisture loss in Formulation Example 1 and Comparative Formulation Example 1.

As is apparent from the foregoing, the cosmetic composition according to the present invention exhibits excellent effects on cell moisturization, intercellular moisturization and skin-barrier moisturization. In addition, the cosmetic composition according to the present invention is harmless to the human body and has excellent stability because it uses natural substances.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An emulsion consisting essentially of propylene glycol, glycerine, and the hydrolysate extract obtained by adding a protease to fruit of *Cicer arietinum*, a *Rhododendron chrysanthum* leaf extract and *Tricholoma matsutake* extract.

* * * * *